(12) United States Patent
Kamon et al.

(10) Patent No.: US 10,166,678 B2
(45) Date of Patent: Jan. 1, 2019

(54) SURGICAL ROBOT AND METHOD FOR CONTROLLING THE SAME

(71) Applicant: KAWASAKI JUKOGYO KABUSHIKI KAISHA, Kobe-shi, Hyogo (JP)

(72) Inventors: Masayuki Kamon, Akashi (JP); Kenji Noguchi, Kobe (JP)

(73) Assignee: KAWASAKI JUKOGYO KABUSHIKI KAISHA, Kobe (JP)

(*) Notice: Subject to any disclaimer, the term of this patent is extended or adjusted under 35 U.S.C. 154(b) by 0 days.

(21) Appl. No.: 14/655,456

(22) PCT Filed: Dec. 25, 2013

(86) PCT No.: PCT/JP2013/084646
§ 371 (c)(1),
(2) Date: Jun. 25, 2015

(87) PCT Pub. No.: WO2014/104087
PCT Pub. Date: Jul. 3, 2014

(65) Prior Publication Data
US 2015/0342689 A1    Dec. 3, 2015

(30) Foreign Application Priority Data
Dec. 25, 2012   (JP) ................. 2012-281179

(51) Int. Cl.
*A61B 19/00* (2006.01)
*B25J 9/16* (2006.01)
(Continued)

(52) U.S. Cl.
CPC ............. *B25J 9/1674* (2013.01); *A61B 34/30* (2016.02); *A61B 34/37* (2016.02); *A61B 34/74* (2016.02);
(Continued)

(58) Field of Classification Search
CPC ......... A61B 34/20; A61B 34/25; A61B 34/30; A61B 34/37; A61B 34/70; A61B 34/74; A61B 34/76; A61B 34/77
(Continued)

(56) References Cited

U.S. PATENT DOCUMENTS

| 6,496,756 B1 | 12/2002 | Nishizawa et al. |
| 2003/0097060 A1 | 5/2003 | Yanof et al. |

(Continued)

FOREIGN PATENT DOCUMENTS

| JP | 2003-079638 A | 3/2003 |
| JP | 2009-525097 A | 7/2009 |

OTHER PUBLICATIONS

Mar. 11, 2014 International Search Report issued in International Patent Application No. PCT/JP2013/084646.
(Continued)

*Primary Examiner* — Allen Porter, Jr.
(74) *Attorney, Agent, or Firm* — Oliff PLC

(57) ABSTRACT

It is an object to provide a surgical robot which can enhance flexibility of treatment while ensuring sufficient safety of a surgery. The surgical robot has a robot body, an input unit for inputting control information of the robot body, a control unit for controlling the robot body based on the control information input to the input unit, an input side abnormality detection unit for detecting abnormality of an operator, an output side abnormality detection unit for detecting abnormality of a surgery state, an abnormality countermeasure unit for dealing with the abnormality of the surgery state detected by the output side abnormality detection unit, contents of an abnormality countermeasure action being changed based on a detection result of the input side abnormality detection unit.

16 Claims, 1 Drawing Sheet

(51) Int. Cl.
   *A61B 34/30*   (2016.01)
   *A61B 34/37*   (2016.01)
   *A61B 34/00*   (2016.01)
   A61B 17/00   (2006.01)
   A61B 18/00   (2006.01)
   A61B 90/00   (2016.01)

(52) U.S. Cl.
   CPC ... *B25J 9/1689* (2013.01); *A61B 2017/00123* (2013.01); *A61B 2018/00303* (2013.01); *A61B 2090/065* (2016.02)

(58) Field of Classification Search
   USPC .......................................... 606/130; 700/245
   See application file for complete search history.

(56) References Cited

U.S. PATENT DOCUMENTS

| | | |
|---|---|---|
| 2007/0078484 A1 | 4/2007 | Talarico et al. |
| 2008/0046122 A1 | 2/2008 | Manzo et al. |
| 2010/0160728 A1 | 6/2010 | Yoshie |
| 2012/0071892 A1 | 3/2012 | Itkowitz et al. |
| 2012/0158011 A1 | 6/2012 | Sandhu et al. |

OTHER PUBLICATIONS

Jun. 30, 2015 International Preliminary Report on Patentability issued in International Patent Application No. PCT/JP2013/084646.
Jul. 4, 2016 Search Report issued in European Patent Application No. 13868655.5.

SURGICAL ROBOT AND METHOD FOR CONTROLLING THE SAME

TECHNICAL FIELD

The present invention relates to a surgical robot on which a medical instrument is mounted so as to support a surgery and a control method thereof.

BACKGROUND ART

Conventionally, a surgical robot of a master/slave system in which a detection switch for detecting abnormality of an operator is provided to an input unit for inputting control information of a master side, namely a robot body, is proposed (Patent Document 1).

In this conventional surgical robot, the robot is stopped or held in position, and the automatic operation and manual operation are switched, in accordance with the detection state of the detection switch.

Also, one of the conventionally proposed surgical robots actuates a warning buzzer when pressure is detected by a piezoelectric film on the outer peripheral wall surface of a trocar which is pierced into the body (Patent Document 2).

RELATED ART DOCUMENTS

Patent Documents

[Patent Document 1] Japanese Unexamined Patent Application Publication (Translation of PCT Application) No. 2009-525097
[Patent Document 2] Japanese Patent Application Laid-Open No. 2003-79638

SUMMARY OF INVENTION

Problems to be Solved by the Invention

However, in the conventional surgical robot (Patent Document 1), the robot may not necessarily need to be stopped or the like, and in some cases, it may be enough to raise a safety factor with respect to a patient while continuing control even when an operator takes his/her hand off the input unit and the detection switch detects abnormality.

However, as the conventional surgical robot is configured to stop the robot or the like uniformly in accordance with the detection state of the detection switch, an approach to raise a safety factor with respect to a patient while continuing control as mentioned above cannot be performed.

Also, in the conventional surgical robot (Patent Document 2), there is a problem that the degree of freedom in treatment by an operator is limited as the buzzer actuates due to a uniform abnormality judgment even when an operator intentionally moves the body of a patient slightly not by erroneous operation.

The present invention is made taking into account the above-mentioned problems of a conventional technique to provide a surgical robot capable of enhancing the degree of freedom in treatment and a control method thereof.

Means for Solving the Problems

In order to solve the above-mentioned problems, a surgical robot according to the present invention includes a robot body on which a medical instrument is mounted; an input unit configured to input a control information of the robot body; a control unit configured to control the robot body based on the control information input to the input unit; an input side abnormality detection unit configured to detect an abnormality of an operator; an output side abnormality detection unit configured to detect an abnormality of a surgery state with the medical instrument, an abnormality countermeasure unit configured to deal with the abnormality of the surgery state detected by the output side abnormality detection unit, the abnormality countermeasure unit being configured to change a content of an abnormality countermeasure action based on a detection result of the input side abnormality detection unit.

Also, it is preferable that the abnormality countermeasure unit has a function of changing a start reference of the abnormality countermeasure action by the abnormality countermeasure unit based on the detection result of the input side abnormality detection unit.

Also, it is preferable that the abnormality countermeasure unit has a plurality of thresholds for a start reference of the abnormality countermeasure action by the abnormality countermeasure unit in advance and a function of selecting a threshold to be applied from the plurality of thresholds based on the detection result of the input side abnormality detection unit.

Also, it is preferable that the input side abnormality detection unit is provided to the input unit.

Also, it is preferable that the input unit includes a handle configured to be operated by the operator, and the input side abnormality detection unit includes an input side detector provided to the handle in order to detect the abnormality of the operator.

Also, it is preferable that the input side abnormality detection unit has a plurality of input side detectors configured to detect the abnormality of the operator, and the control unit is configured to change the content of the abnormality countermeasure by the abnormality countermeasure unit based on a plurality of detection results from the plurality of input side detectors.

Also, it is preferable that the output side abnormality detection unit has an output side detector configured to detect an influence of the medical instrument on a body of a patient.

Also, it is preferable that the output side detector is configured to detect a pressure which is applied by the medical instrument on a contact portion with the body of the patient.

Also, it is preferable that the output side detector is configured to detect a displacement amount that the medical instrument displaces a contact portion with the body of the patient.

Also, it is preferable that the abnormality countermeasure unit includes a notification unit configured to notify the abnormality of the surgery state.

Also, it is preferable that the abnormality countermeasure unit includes a control mode change unit configured to change a control mode of the robot body.

Also, it is preferable that the control mode change unit is configured to change a speed limit of an action of the robot body.

Also, it is preferable that the control mode change unit is configured to switch between a mode which drives the medical instrument according to the control information from the input unit and a mode which drives the medical instrument in a direction that an external force from a body of a patient acting on the medical instrument is parried.

Also, it is preferable that the control mode change unit has a switch function for switching to an automatic control mode in which the robot body is automatically controlled so as to minimize an influence of the medical instrument on a body of a patient.

In order to solve the above-described problems, a control method of a surgical robot having a robot body on which a medical instrument is mounted according to the present invention includes a control information input step of inputting a control information of the robot body; a control step of controlling the robot body based on the control information; an input side abnormality detection step of detecting an abnormality of an operator; an output side abnormality detection step of detecting an abnormality of a surgery state with the medical instrument; and an abnormality countermeasure step of dealing with the abnormality of the surgery state detected in the output side abnormality detection step, a content of an abnormality countermeasure action being changed based on a detection result of the input side abnormality detection step.

Also, it is preferable that the abnormality countermeasure step changes a start reference of the abnormality countermeasure action in the abnormality countermeasure step based on the detection result of the input side abnormality detection step.

Also, it is preferable that the abnormality countermeasure step has a plurality of thresholds for the start reference of the abnormality countermeasure action in the abnormality countermeasure step in advance, and selects a threshold to be applied from the plurality of thresholds based on the detection result of the input side abnormality detection step.

Note that, the term "abnormality" used in the present description represents a state to be distinguished from a normal state with respect to some indices (ON/OFF of a sensor, pressure output by a sensor, and the like) which are detectable by a detection unit, and the meaning thereof is not necessarily the same as the literal meaning of "abnormality".

Advantageous Effect of the Invention

According to the surgical robot and the control method thereof according to the present invention, the content of the abnormality countermeasure by the abnormality countermeasure unit is changed based on the detection result of the input side abnormality detection unit so that the safety of surgery can be sufficiently secured while enhancing flexibility of treatment.

EMBODIMENT OF THE INVENTION

Figure 1:
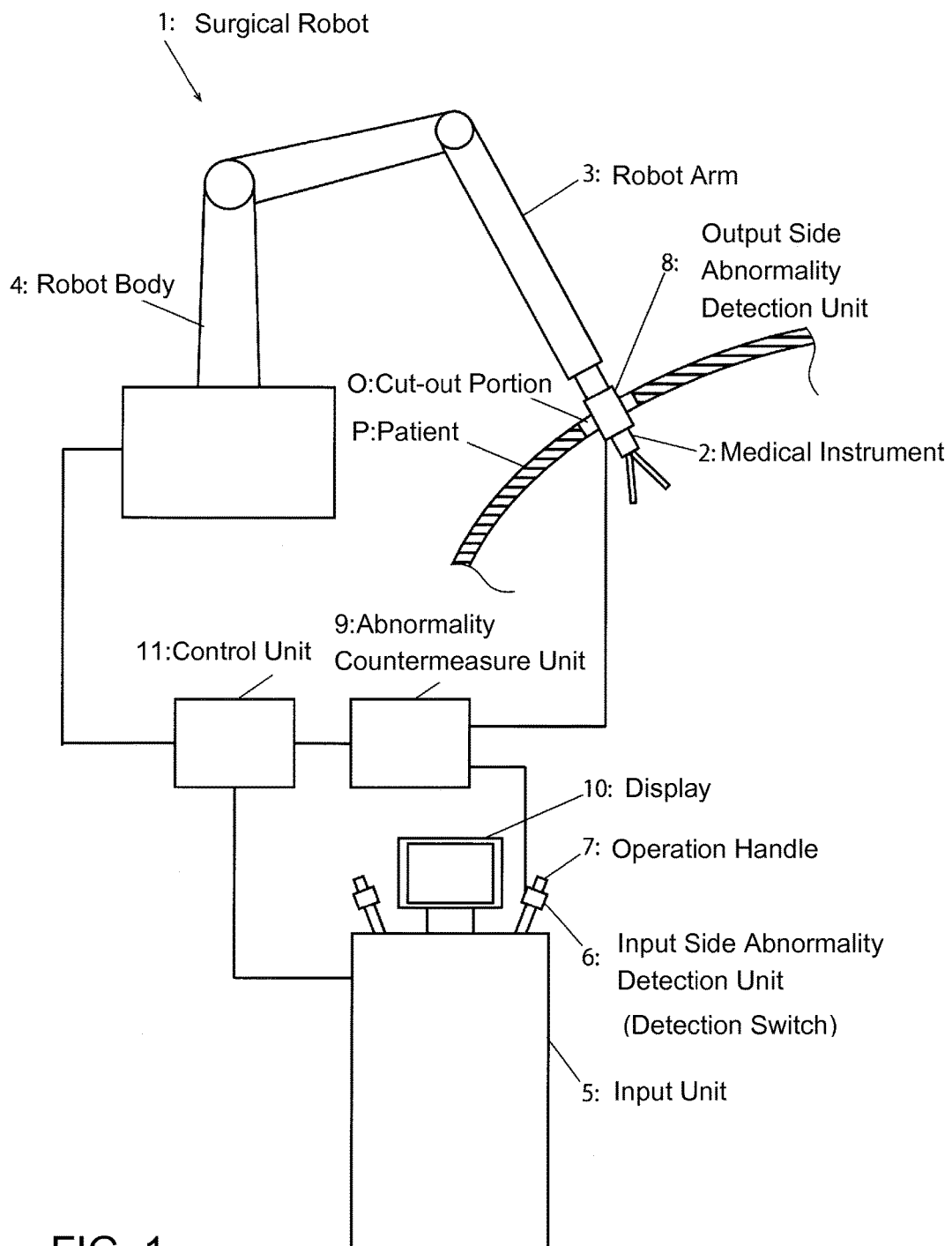
FIG. 1 is a schematic view illustrating a surgical robot according to an embodiment of the present invention.

Hereunder, the surgical robot and its control method according to an embodiment of the present invention will be described referring to FIG. 1.

A surgical robot 1 of the embodiment has a robot body 4 provided with a robot arm 3 having a tip end on which a medical instrument 2 is mounted. Control information of the robot body 4 is input by an input unit 5. The medical instrument may be, but not limited to, a forceps, a cautery, an electric scalpel, an imaging apparatus or the like.

The input unit 5 is provided with an input side abnormality detection unit 6 for detecting abnormality of an operator (a medical doctor). Specifically, a detection switch (an input side detector) is provided to an operation handle 7 which is part of the input unit 5.

The detection switch (input side detector) may be what detects the presence/absence of gripping force of the operator, what detects the presence/absence of contact with the operator' hand, what is particularly provided with a trigger and a switch for telling that the operator is intentionally gripping the operation handle 7, or the like.

Alternatively, when using a head mount display, the detection switch may be what detects that the head mount display is displaced from the regular position Namely, the input side abnormality detection unit 6 is not limited to the detection switch attached to the operation handle 7 and anything which outputs information contributing to judging whether or not the operator concentrates on a surgery, for example, can be used.

Also, all or part of the above-mentioned various detection switches or the like may be combined properly so as to detect a plurality of states, not only the two states, and set thresholds for each of the states.

The surgical robot 1 of the present embodiment is further provided with an output side abnormality detection unit 8 for detecting abnormality of the surgery state with the medical instrument 2. Specifically, an output side detector for detecting influence of the medical instrument 2 on the body of the patient P is provided to the medical instrument 2. The output side abnormality detection unit 8 may be provided to the medical instrument 2 or the robot arm 3, or may be provided independently.

The output side detector which configures the output side abnormality detection unit 8 may be what detects a pressure applied by the medical instrument 2 on a contact portion (particularly, a cut-out portion O) with the body of the patient P (a film sensor or the like), what detects a displacement amount that the medical instrument 2 which displaces the contact portion (particularly, the cut-out portion O) with the body of the patient P, or the like. Or, what detects the approach/contact of the robot arm 3 to/with the patient P or a surgery assistant can also be used.

Namely, the output side abnormality detection unit 8 may be anything so long as it can estimate an influence of the medical instrument 2 on the patient P, for example.

Also, a portion to be detected by the output side abnormality detection unit 8 is not limited to the cut-out portion O, and reaction force applied to the robot arm 3 and the tip end of the medical instrument 2 may be also detected. Or, sensors may be arranged to a plurality of locations which possibly make contact with the patient P so as to comprehensively judge the influence on the patient P.

The surgical robot 1 of the present embodiment is further provided with an abnormality countermeasure unit 9 for dealing with abnormality of a surgery state detected by the output side abnormality detection unit 8. An example of the abnormality countermeasure unit 9 is a notification unit which is configured to notify that abnormality of the surgery state occurs.

The notification unit may be what displays the abnormal state on a display 10, for example, and what is by various methods such as sound, lighting of an alarm light, or applying vibrations to the operation handle 7 can be employed. Namely, the notification unit may be anything so long as it can notify abnormality.

Also, another example of the abnormality countermeasure unit 9 stops the operation of the robot body 4. Namely, the operation of the robot body 4 is stopped and brought into a locked state when abnormality is detected by the output side abnormality detection unit 8.

Namely, the abnormality countermeasure unit 9 may be anything so long as it minimizes the direct and indirect influence on the body of the patient P in response to the abnormal state of a surgery.

A control unit 11 of the present embodiment controls the robot body 4 based on the control information input by the input unit 5 and also sends display contents of the display 10 or the like to the input unit 5.

Also, the abnormality countermeasure unit 9 is configured so as to change contents of the abnormality countermeasure based on the detection result of the input side abnormality detection unit 6. More specifically, the abnormality countermeasure unit 9 has a plurality of thresholds for the start reference of an abnormality countermeasure action in advance and has a function of selecting a threshold to be applied from the plurality of thresholds based on the detection result of the input side abnormality detection unit 6.

For example, the abnormality countermeasure unit 9 judges whether the detection switch (input side detector) 6 provided to the operation handle 7 is ON (normal) or OFF (abnormal). In case of ON, the operator is supposed to concentrate on a surgery, and therefore a threshold for a detection value from the output side abnormality detection unit 8 is set to a relatively high level.

Here, the threshold for the detection value from the output side abnormality detection unit 8 serves as the start reference (trigger) for starting the abnormality countermeasure action (abnormality notification and/or robot stop) by the abnormality countermeasure unit 9 when the detection value exceeds the threshold.

Accordingly, by setting the threshold for the detection value from the output side abnormality detection unit 8 to the relatively high level, the abnormality countermeasure action (abnormality notification and/or robot stop) by the abnormality countermeasure unit 9 is started relatively insensibly (slowly).

On the other hand, when the detection switch (input side detector) 6 provided to the operation handle 7 is OFF (abnormal), an operator is supposed not to concentrate on a surgery, and therefore a threshold for a detection value from the output side abnormality detection unit 8 is set to a relatively low level.

By setting the threshold for the detection value from the output side abnormality detection unit 8 to the relatively low level in this manner, the abnormality countermeasure action (abnormality notification and/or robot stop) by the abnormality countermeasure unit 9 is started relatively sensitively (quickly) so as to improve the safety level.

As described above, when the detection switch (input side detector) 6 is ON and the operator is supposed to concentrate on the surgery, the surgery can be continued without causing abnormal notification and/or a robot stop even when, for example, the operator slightly moves the body of the patient P intentionally, by performing the abnormality countermeasure action (abnormality notification and/or robot stop) by the abnormality countermeasure unit 9 relatively insensibly (slowly).

On the other hand, when the detection switch (input side detector) 6 is ON and the operator is supposed not to concentrate on the surgery, the abnormal countermeasure action (abnormality notification and/or robot stop) may be performed relatively sensitively (quickly) so as to surely deal with the abnormal state of the surgery.

Note that the above-mentioned abnormality countermeasure unit 9 may be configured to deal with the abnormality so as to divide the same into a plurality of levels. For example, it may be configured to divide the abnormality into three levels of a safe level, an intermediate level, and a dangerous level, so that the display 10 shows "safe" in blue, "intermediate" in yellow, and "dangerous" in red, respectively.

Here, provided that a threshold between "safe" and "intermediate" is a first threshold and a threshold between "intermediate" and "dangerous" is a second threshold, when the detection switch (input side detector) 6 is in two states of ON/OFF, the first and second thresholds in case of switch ON and the first and second thresholds in case of switch OFF are set respectively (namely, four thresholds are set). Note that a part of the thresholds which are set in this manner possibly become the same value.

Further, the abnormality countermeasure unit 9 can be provided with a control mode change unit which is configured to change the control mode of the robot along with (or instead of) the notification unit which is configured to notify abnormality to the operator.

For example, the speed limit on actions of the robot 4 may be set relatively high at the safe level, and relatively low at the dangerous level so as to change the safety factor for the patient P.

Also, the control mode change unit can be configured to switch between a mode for driving the medical instrument 2 according to the control information from the input unit 5 and a mode for driving the medical instrument 2 in the direction that external force from the body of the patient P which acts on the medical instrument 2 is parried.

Also, the control mode change unit can be provided with a switch function for switching to an automatic control mode for controlling the robot body 4 so as to minimize the influence of the medical instrument 2 on the body of the patient P based on image information on a surgical site and various sensor information.

Here, "so as to minimize the influence on the body" means a countermeasure of lowering a pressure of the cut-out portion O of the patient P on the side wall of the body or a countermeasure of moving the medical instrument 2 close to internal organs or the like, if any, away from the internal organs or the like.

Also, the input side abnormality detection unit 6 can be provided with a plurality of input side detectors for detecting abnormality of the operator. In this case, the control unit 11 is configured to change contents of the abnormality countermeasure by the abnormality countermeasure unit 9 based on respective detection results from the plurality of detectors according to detection results of the output side abnormality detection unit 8.

In the description of the present embodiment, an example that the abnormality countermeasure unit 9 is connected to the control unit 1 is disclosed, assuming that the abnormality countermeasure unit 9 sends an abnormality countermeasure signal to the control unit 11 so as to make the robot body 4 perform an abnormality countermeasure action (locking the robot body 4, for example) or make the input unit 5 perform an abnormality countermeasure action (displaying a warning on the display 10, for example).

As a modification of the above-described embodiment, for example when the abnormality countermeasure unit 9 deals with abnormality singly and independently from the control unit 11 (notifying occurrence of abnormality with a buzzer, for example), the abnormality countermeasure unit 9 and the control unit 11 are possibly not connected to each other. Further, the control unit 11 and the abnormality countermeasure unit 9 may be realized as a function in a program respectively and may include another unit such as an image process unit.

As described above, according to the surgical robot 1 of the present embodiment, contents of the abnormal countermeasure by the abnormality countermeasure unit 9 are changed based on the detection results of the input side abnormality detection unit 6, and therefore the flexibility of treatment can be enhanced while ensuring sufficient safety of a surgery.

Note that the configuration of the present invention is not necessarily essential when a high flexibility of treatment is ensured by a configuration, a method or the like other than the present invention.

EXPLANATION OF REFERENCE NUMERALS

1 . . . surgical robot
2 . . . medical instrument
3 . . . robot arm
4 . . . robot body
5 . . . input unit
6 . . . input side abnormality detection unit (detection switch)
7 . . . operation handle
8 . . . output side abnormality detection unit
9 . . . abnormality countermeasure unit
10 . . . display
11 . . . control unit
O . . . cut-out portion of patient's body
P . . . patient

The invention claimed is:

1. A surgical robot comprising:
a robot body on which a medical instrument is mounted;
an operation handle configured to input a control information of the robot body;
a control processor configured to control the robot body based on the control information input to the operation handle;
an input side abnormality detecting switch configured to detect an abnormality of an operator;
an output side abnormality detecting sensor configured to detect an abnormality of a surgery state with the medical instrument; and
an alarm configured to perform an abnormality countermeasure action if a detection value from the output side abnormality detecting sensor exceeds a threshold value,
wherein the surgical robot is configured so that the threshold value is set to a first value if the abnormality of the operator is detected by the input side abnormality detecting switch, and is set to a second value, different from the first value, if the input side abnormality detecting switch does not detect the abnormality of the operator.

2. The surgical robot according to claim 1, wherein the input side abnormality detecting switch is coupled with the operation handle.

3. The surgical robot according to claim 2, wherein the operation handle is configured to be operated by the operator and the input side abnormality detecting switch is provided to the handle.

4. The surgical robot according to claim 1, further comprising a plurality of input side abnormality detecting switches, each input side abnormality detecting switch configured to detect the abnormality of the operator at a different magnitude of detection, and wherein the control processor is configured to change the content of the abnormality countermeasure based on a plurality of detection results from the plurality of input side abnormality detecting switches.

5. The surgical robot according to claim 1, wherein the output side abnormality detecting sensor is configured to detect an influence of the medical instrument on a body of a patient.

6. The surgical robot according to claim 5, wherein the output side abnormality detecting sensor is configured to detect a pressure which is applied by the medical instrument on a contact portion with the body of the patient.

7. The surgical robot according to claim 5, wherein the output side abnormality detecting sensor is configured to detect a displacement amount that the medical instrument displaces a contact portion with respect to the body of the patient.

8. The surgical robot according to claim 5, wherein the alarm includes a notification device configured to notify the abnormality of the surgery state.

9. The surgical robot according to claim 1, wherein the alarm is configured to change a control mode of the robot body.

10. The surgical robot according to claim 9, wherein the alarm is configured to change a speed limit of an action of the robot body.

11. The surgical robot according to claim 9, wherein the alarm is configured to switch between a mode which drives the medical instrument according to the control information from the operation handle and a mode which drives the medical instrument in a direction that an external force from a body of a patient acting on the medical instrument is parried.

12. The surgical robot according to claim 9, wherein the alarm is configured to switch an automatic control mode in which the robot body is automatically controlled so as to minimize an influence of the medical instrument on a body of a patient.

13. The surgical robot according to claim 1, wherein the second value of the threshold value is higher than the first value of the threshold value.

14. A control method of a surgical robot which has a robot body on which a medical instrument is mounted, the control method comprising:
inputting, with an operation handle, control information of the robot body;
controlling, with a control processor, the robot body based on the control information input to the operation handle;
detecting, by an input side abnormality detecting switch, an abnormality of an operator based on the input control information inputted by the operation handle;
controlling the robot body and detecting, by an output side abnormality detecting sensor, an abnormality of a surgery state with the medical instrument and setting a detection value based on a magnitude of the detected abnormality of the surgery state; and
performing an abnormality countermeasure action for the surgical robot upon the detection value of the detected abnormality of the surgery state exceeding a threshold value,
wherein the surgical robot is configured so that the threshold value is set to a first value if the abnormality of the operator is detected, and is set to a second value, different from the first value, if the abnormality of the operator is not detected.

15. The control method according to claim 14, wherein the second value of the threshold value is higher than the first value of the threshold value.

16. The control method according to claim 14, wherein the abnormality countermeasure action is at least one of: locking the robot body and displaying a warning on a display.

\* \* \* \* \*